United States Patent [19]

Graney

[11] Patent Number: 5,585,355
[45] Date of Patent: Dec. 17, 1996

[54] METHOD FOR INCREASING BLOOD-OCULAR BARRIER PERMEABILITY WITH PERMEABILIZER PEPTIDES

[75] Inventor: William F. Graney, Cambridge, Mass.

[73] Assignee: Alkermes, Inc., Cambridge, Mass.

[21] Appl. No.: 306,873

[22] Filed: Sep. 12, 1994

Related U.S. Application Data

[63] Continuation-in-part of Ser. No. 232,526, Apr. 22, 1994, abandoned.

[51] Int. Cl.⁶ .......................... A61K 38/00; A61K 38/04; C07K 5/00; C07K 7/00
[52] U.S. Cl. .......................... 514/15; 530/314; 530/328
[58] Field of Search .............................. 514/15; 530/314, 530/328; 424/9, 1.1, 2

[56] References Cited

U.S. PATENT DOCUMENTS

| | | | |
|---|---|---|---|
| 4,923,963 | 5/1990 | Stewart et al. | 530/314 |
| 5,112,596 | 5/1992 | Malfroy-Camine | 424/2 |
| 5,162,497 | 11/1992 | Coy et al. | 530/314 |
| 5,268,164 | 12/1993 | Kozarich et al. | 424/9 |

FOREIGN PATENT DOCUMENTS

| | | | |
|---|---|---|---|
| 0370656 | 5/1990 | European Pat. Off. | A61K 37/02 |
| 0529499A1 | 3/1993 | European Pat. Off. | |
| WO89/09231 | 10/1989 | WIPO . | |
| 92/18529 | 10/1992 | WIPO . | |

OTHER PUBLICATIONS

Cole, D. F., *Exp. Eye. Res.*, vol. 19, No. 6, pp. 591–607, 1974.
Kuppersmith et al., Implications of the Blood–Brain–Barrier and its Manipulation, E. A. Neuwelt, M.D. ed., pp. 369–390, 1989.
Greenwood, J., "Mechanisms of blood–brain barrier breakdown", *Neuroradiology*, 33(2) : 95–100 (1991).
Cole, D. F., "The Site of Breakdown of the Blood–Aqueous Barrier under the Influence of Vaso–dilator Drugs", *Exp. Eye Res.*, 19(6) : 591–607 (1974).
Bynke, G., et al., "Bradykinin Contracts The Pupillary Sphincter and Evokes Ocular Inflammation Through Release of Neuronal Substance P", *Eur. J. Pharmacol.*, 91(4) : 469–475 (Abstract only) (1983).
Kaufman, P. L., et al., "Effect of Serotonin, Histamine and Bradykinin on Outflow Facility Following Ciliary Muscle Retrodisplacement in the Cynomolgus Monkey", *Exp. Eye Res.*, 35(2) : 91–199 (Abstract only) (1982).
Ferrari–Dileo, G., et al., "Angiotensin–Converting Enzyme in Bovine, Feline, and Human Ocular Tissues", *Invest. Ophthalmol. Vis. Sci.*, 29(6) : 876–881 (Abstract only) (1988).
Yokoyama, K., et al., "Implication of Polymodal Receptor Activities in Intraocular Pressure Elevation By Neurogenic Inflammation", *Jpn. J. Ophthalmol.*, 34(2) : 245–255 (Abstract only) (1990).

Kupersmith, M. J. and Shakib, M., "The Blood–Ocular Barrier". In *Implications of the Blood–Brain Barrier and Its Manipulation*, E. A. Neuwelt, M.D. ed. (NY: Plenum Publishing ), pp. 369–390 (1989).
Bradbury, M. W. B. and Lightman, S. L., "The Blood–Brain Interface", *Eye*, 4:249–254 (1990).
Alm, A., "Ocular Circulation". In *Adlers Physiology of the Eye 9th Ed.*, W. M. Hart, Jr., ed. (St. Louis, MO: Mosbey–Year Book Inc.), pp. 198–227 (1992).
Stewart, P. A. and Tuor, U. I., "Blood–Eye Barriers in the Rat: Correlation of Ultrastructure With Function", *J. of Comparative Neurol.*, 340:566–576 (1994).Gratton et al., *J. Physiol.*, vol. 446, p. 508P, Nov. 1991.
Mataix Sanjuan et al., *Chemical Abstrat*, vol. 119, p. 3, 1993, Ab No.: 85149d.
Zlokovic, B. V. et al., "An In Situ Perfused Guinea–pig Eye Model for Blood–Ocular Transport Studies: Application to Amino Acids", *Exp. Eye Res.*, 54:471–477 (1992).
Novack, G. D. et al., "The Blood–Aqueous and Blood–Brain Barriers to Permeability", *Am. J. of Ophthalmology* (Editorial) 105(4): 412–416 (Apr. 1988).
Frank, J. A. et al., "Opening of Blood–Ocular Barrier Demonstrated by Contrast–Enhanced MR Imaging", *J. of Computer Assisted Tomography* 10(6): 912–916 (Nov.–Dec. 1986).
Enea, N. A. et al., "Histamine $H_1$ Receptors Mediate Increased Blood –Retinal Barrier Permeability in Experimental Diabetes", *Arch Ophthalmol* 107:270–274 (Feb. 1989).
BenEzra, D. et al., "Ocular Penetration of Cyclosporine A in the Rat Eye", *Arch Ophthalmol* 108:584–587 (Apr. 1990).
Kyle, D. J. et al., "Probing the Bradykinin Receptor: Mapping the Geometric Topography Using Ethers of Hydroxyproline in Novel Peptides", *J. Med. Chem.* 34(8) : 2649–2653 (1991).
Drapeau, G. et al., "Synthesis of Bradykinin Analogs", *Methods in Enzymology* 163:263–272 (1988).
Kyle, D. J. et al., "Design and Conformational Analysis of Several Highly Potent Bradykinin Receptor Antagonists", *J. Med. Chem.*, 34(3) : 1230 –1233 (1991).
Unterberg, A. et al., "The Kallikrein–Kinin System as Mediator in Vasogenic Brain Edema Part I: Cerebral Exposure to Bradykinin and Plasma", *J. Neurosurg.* 61:87–96 (Jul. 1984).
Wahl, M. et al., "Effects of Bradykinin on Cerebral Haemodynamics and Blood –Brain Barrier Function", In: Peptidergic Mechanisms in Cerebral Circulation (Edwinssen and McCulloch, Eds.) Chichester, Herwood, pp. 166.

(List continued on next page.)

*Primary Examiner*—Avis M. Davenport
*Attorney, Agent, or Firm*—Hamilton, Brook, Smith & Reynolds, P.C.

[57] ABSTRACT

The permeability of the blood-ocular barrier to therapeutic or diagnostic agents in the bloodstream of a host is increased by administering a permeabilizer peptide, preferably bradykinin or a bradykinin analogue, into the bloodstream of a host. The invention provides methods of treatment or diagnosis of ocular diseases by administration of a permeabilizer peptide, such as permeabilizer A-7, in combination with a therapeutic or diagnostic agent.

12 Claims, 5 Drawing Sheets

OTHER PUBLICATIONS

Wahl, M. et al., "Mediators of Blood–Brain Barrier Dysfunction and Formation of Vasogenic Brain Edema", *J. Cereb. Blood Flow Metab 634 (1988)*.

Raymond, J. J. et al., "Pharmacological Modification of Bradykinin Induced Breakdown of the Blood–Brain Barrier", *Can. J. Neurol. Sci.*, 13(3): 214–220 (Aug. 1986).

Saria, A. et al., "Vascular Protein Leakage in Various Tissues Induced by Substance P, Capsaicin, Bradykinin, Serotonin, Histamine and by Antigen Challenge", *Naunyn–Schniedeberg's Arch. Pharmacol.*, 324:2 (1983).

Marceau, F. et al., "Pharmacology of Kinins: Their Relevance to Tissue Injury and Inflammation", *Gen. Pharmacol.*, 14(2): 209–229.

Rhaleb, N.–E. et al., "Structure–Activity Studies on Bradykinin and Related Peptides: Agonists", *Br. J. Pharmacol.*, 99(3): 445–448 (1990).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( C ) INDIVIDUAL ISOLATE: Synthesized ( i x ) FEATURE:
        ( A ) NAME/KEY: Modified-site
        ( B ) LOCATION: 3
        ( D ) OTHER INFORMATION: /label= other
            / note= "hydroxyproline"

( i x ) FEATURE:
        ( A ) NAME/KEY: Modified-site
        ( B ) LOCATION: 5
        ( D ) OTHER INFORMATION: /label= other
            / note= "thienylalanine"

( i x ) FEATURE:
        ( A ) NAME/KEY: Modified-site
        ( B ) LOCATION: 8
        ( D ) OTHER INFORMATION: /label= other
            / note= "substituent is a 4-methyl group"

( i x ) FEATURE:
        ( A ) NAME/KEY: Modified-site
        ( B ) LOCATION: 8..9
        ( D ) OTHER INFORMATION: /label= other
            / note= "reduced peptide bond"

( x i ) SEQUENCE DESCRIPTION: SEQ ID NO:1:

Arg  Pro  Xaa  Gly  Xaa  Ser  Pro  Tyr  Arg
    1                          5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( x ) PUBLICATION INFORMATION:
        ( A ) AUTHORS: A.L. Lehninger
        ( B ) TITLE: Biochemistry
        ( C ) PAGES: 97
        ( D ) DATE: 1975

( x i ) SEQUENCE DESCRIPTION: SEQ ID NO:2:

Arg  Pro  Pro  Gly  Phe  Ser  Pro  Phe  Arg
    1                          5

METHOD FOR INCREASING BLOOD-OCULAR BARRIER PERMEABILITY WITH PERMEABILIZER PEPTIDES

RELATED APPLICATION

This application is a continuation-in-part of U.S. application Ser. No. 08/232,526, filed Apr. 22, 1994 and now abandoned.

BACKGROUND OF THE INVENTION

The blood-ocular barrier (BOB) provides a shield for the ocular tissues and fluids, preventing the transport of certain molecules from the plasma into the eye. This is generally a favored feature of the BOB, except when the transport of therapeutic or diagnostic agents to the eye is desired. The BOB is comprised of capillary endothelial cells connected by tight junctions. Although alterations in the permeability of the barrier may occur in certain diseases, as well as from trauma, surgery or certain pharmacologic agents, it is generally not sufficient to permit adequate quantities of a therapeutic agent into the eye.

Currently, agents are administered for delivery to the eye by a number of methods including systemic administration (intravenous), local application of an agent-containing solution, placement of a porous component in contact with the eye for sustained release of an agent, or insertion of an implant containing an agent. These delivery methods are often inadequate due to the limited ability of the agent itself to penetrate the BOB. In other cases, agents are administered by direct injection into the eye. This means is inadequate due to a high level of discomfort, risk of injury, and expense of treatment.

The need exists for an effective and non-invasive means for delivering adequate quantities of a therapeutic or diagnostic agent into the eye and across the BOB in order to provide better treatment and diagnosis of ocular diseases.

SUMMARY OF THE INVENTION

The present invention pertains to a method of increasing the permeability of the blood-ocular barrier of a host to a molecule present in the host's bloodstream. The method comprises administration to the host of an effective amount of a permeabilizer peptide wherein the peptide comprises bradykinin or an analogue of bradykinin. In a preferred embodiment, the bradykinin analogue, referred to herein as A-7, has the core sequence Arginine-Proline-Hydroxyproline-Glycine-Thienylalanine-Serine-Proline-4-Me-Tyrosine-(CH$_2$NH)Arginine (SEQ. I.D. NO. 1) from N-terminus to C-terminus where CH$_2$NH denotes a reduced peptide bond between the 4-Me-tyrosine and arginine amino acids. Conformational analogues of the A-7 sequence are also preferred permeabilizers useful in this invention provided they have the property of increasing the permeability of the BOB.

The molecule to be delivered to the eye can be an endogenous molecule residing in the bloodstream or an exogenous molecule that is co-administered sequentially or simultaneously with the permeabilizer peptide.

An advantage of the present invention is that it provides a practical means of increasing the permeability of the blood-ocular barrier to a co-administered molecule or drug of therapeutic, prophylactic or diagnostic value. The permeabilizer peptide can be administered intravascularly (intravenous or intraarterial), or by any route that permits it to enter the bloodstream of the host. In contrast to methods wherein a drug is directly injected into the eye, or introduced by way of a component placed in contact with the eye for sustained release, intravascular administration is significantly less traumatic, causes less discomfort to the patient and is unlikely to necessitate anaesthesia.

Finally, the invention pertains to methods for delivery of a therapeutic or diagnostic agent into the eye of a patient in need of such treatment comprising co-administering an effective amount of a permeabilizer peptide and an agent to be delivered to the eye in order to effect the permeability of the blood-ocular barrier to the agent of interest.

DETAILED DESCRIPTION OF THE INVENTION

Figure 1:
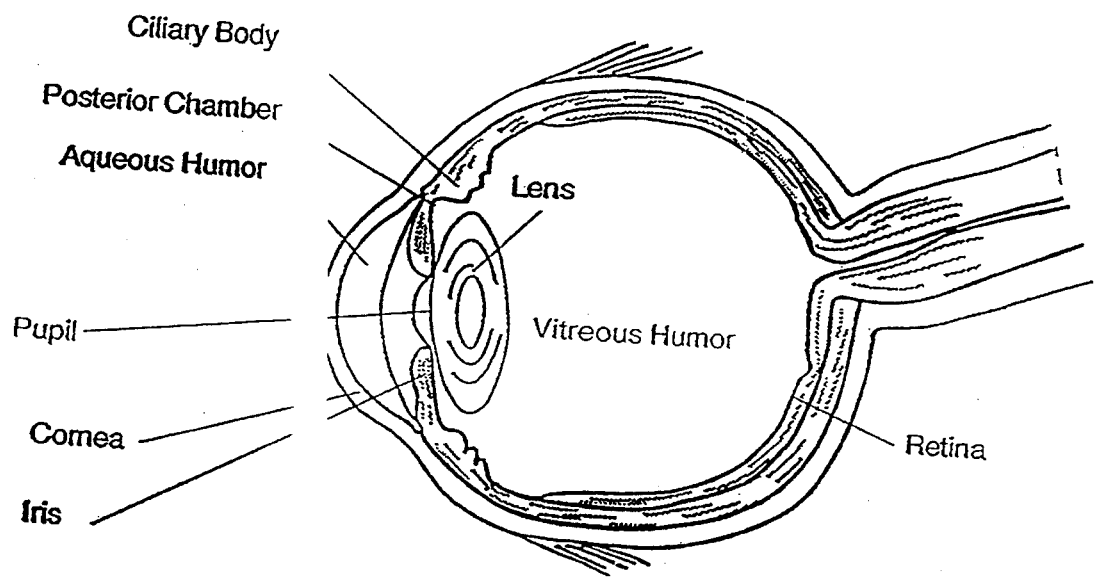
FIG. 1 is a diagram of a human eye.

In general, the BOB can be separated into the blood-aqueous barrier (BAB) and the blood-retinal barrier (BRB). These barriers divide the eye into three chambers (anterior, posterior and vitreous) containing two humors, the aqueous humor and the vitreous humor (FIG. 1). The anterior chamber is anterior to the iris and the posterior chamber extends anteriorly from the vitreous body and comprises the ciliary processes, lens and posterior part of the iris. The vitreous chamber is bounded posteriorly by the retina and anteriorly by the pars plana and contains the vitreous humor.

The cells of the anterior chamber barrier are somewhat different from those in the posterior chamber. The barrier in the anterior chamber is made up of vascular epithelium, basement membrane and iris stroma. The posterior chamber barrier is made up of vascular endothelium, basement membrane, stroma and two layers of ciliary epithelium (Cole et al, 1984, In Davson, H. (ed.) The Eye. Vegetative Physiology and Biochemistry. New York, Academic Press, vol. 1a, p 269; Cunha-Vaz, 1979, Surv. Opthalmol. 23:279). All of these cells appear to be connected by tight junctions.

The barrier protecting the vitreous chamber consists of the ciliary epithelium, the retinal pigment epithelium and the endothelial layer that lines retinal blood vessels. These cells are also connected by tight junctions. However, the retinal vessels have even tighter tight junctions than the BAB.

As used herein, the term "blood-ocular barrier" means the blood-aqueous barrier or the blood-retinal barrier, alone or in combination, as well as any other system of tight junctions within the ocular compartments. The terms "blood-retinal barrier" and "blood-vitreous barrier" can be used interchangeably to describe the barrier protecting the vitreous chamber.

The present invention relates to a method for increasing the permeability of the blood-ocular barrier of a host to a molecule present in the host's bloodstream. By increasing the permeability of the blood-ocular barrier to a molecule of interest, the molecule more readily leaves the bloodstream and enters the interstitial fluids of the eye. The increase in blood-ocular barrier permeability to a molecule of interest in the presence of the permeabilizer peptide provides accessibility of the molecule to the eye in higher relative concentrations than in the absence of the permeabilizer peptide.

For purposes of this invention, a compound is a permeabilizer of the blood-ocular barrier when it significantly increases the permeability of the blood-ocular barrier to a molecule of interest. This effect may operate through a receptor mediated event. The preferred permeabilizers are peptides, peptoids, or peptidomimetics like bradykinin or bradykinin analogues. Bradykinin is a naturally occurring peptide comprised of nine amino acids having the following sequence: Arginine-Proline-Proline-Glycine-Phenylalanine-Serine-Proline-Phenylalanine-Arginine (SEQ. I.D. NO. 2) (Lehninger, A. L., 1975, Biochemistry, p. 97). An analogue is a structural derivative of a parent compound. Analogues of bradykinin can be compounds which are derivatives of the number and/or sequence of amino acids in the bradykinin structure mentioned above which have a similar or enhanced effect on permeability of the blood-ocular barrier. Modification of the bradykinin molecule can be made by changing or modifying peptide bonds, adding C-terminal or N-terminal extensions, etc.

Particularly preferred bradykinin analogues which are permeabilizers of blood-ocular barrier permeability are peptide A-7 and conformational analogues of A-7. A-7 has the following linear amino acid sequence from N-terminus to C-terminus:
Arginine-Proline-Hydroxyproline-Glycine-Thienylalanine-Serine-Proline-4-Me-Tyrosine-($CH_2NH$)Arginine (SEQ. ID NO. 1).

The peptide A-7 differs from a conventional linear amino acid sequence in the following ways: the fifth amino acid is thienylalanine which is similar to phenylalanine but where a thienyl group has replaced the phenyl group; the eighth amino acid is tyrosine which has been substituted with a methyl group at the 4 position; and the peptide bond between the eighth and ninth amino acids has been replaced with a reduced peptide bond isotere, i.e. $CH_2NH$. Peptide, peptoid and peptidomimetic analogues of A-7 are also part of this invention provided they allow the proper conformation in aqueous solution so they effect an increase in permeability of the blood-ocular barrier to molecules of interest. These compositions are termed "conformational analogues" of this embodiment.

The preferred permeabilizer A-7 differs from bradykinin in the following respects: at the third amino acid, hydroxyproline replaces proline; at the fifth amino acid, thienylalanine replaces phenylalanine; at the eighth amino acid, 4-Me-tyrosine replaces phenylalanine; and between the eighth and ninth amino acids, a reduced peptide bond replaces a conventional peptide bond.

Characteristic features of the permeabilizer A-7 or conformational analogues of this invention are important for the permeabilizer A-7 or conformational analogues to allow the proper conformation to effect an increase in the permeability of the blood-ocular barrier to a molecule of interest. Further and more detailed descriptions of modifications that can be made to bradykinin, analogues of bradykinin and permeabilizer A-7 are provided in U.S. Pat. Nos. 5,112,596 and 5,268,164 assigned to the same assignee, the teachings of which are hereby incorporated by reference.

The invention relates to a method for increasing the permeability of the blood-ocular barrier of a host to a molecule present in the host's bloodstream. The host can be any organism which possesses an eye, including mammals, such as humans and domestic animals (e.g., dogs, cats, cows, sheep, goats or horses), as well as animals intended for experimental purposes (e.g., guinea pigs, rats, mice, rabbits).

The molecule in the host's bloodstream can be exogenous to the host. For example, it can be an agent which has a therapeutic effect on an ocular disease or disorder. Examples of ocular diseases and disorders include viral infections, such as AIDS- associated cytomegalovirus (CMV) retinitis, bacterial infections or endopthalmitis (bacterial or fungal infection caused by trauma or surgery), cystoid macular degeneration, diabetic retinopathy, inflammation, or tumors (e.g., retinoblastoma).

Classes of therapeutic agents which can be used in this invention include antibiotics, antiviral agents, anti-inflammatory agents, and chemotherapeutic agents. Examples of antibiotics include cephalosporins, penicillins and quinolines. Examples of antiviral agents include ganciclovir and foscarnet. Examples of anti-inflammatory agents include ketorolac, naproxen or any non-steroidal anti-inflammatory drug (NSAID). Examples of chemotherapeutic agents include carboplatin and cisplatin. The therapeutic agents can also include the prodrug form of an agent which is metabolized to the active form of a drug following administration. The molecules in the host's bloodstream can also be a diagnostic agent, such as an imaging or contrast agent or a dye. Examples of diagnostic imaging agents include substances that are labeled with radioactivity, such as 68Gallium for positron emission tomography (PET) scanning, gadolinium based agents for magnetic resonance imaging (MRI), and $^{99}$Tc-DTPA for Single Photon Emission Computed Tomography (SPECT) scanning. Examples of dyes include fluorescein and indocyanine green.

The invention further pertains to a method of treating cytomegalovirus retinitis in the eye of a patient, comprising administering a therapeutically effective amount of an antiviral agent and an effective amount of a permeabilizer peptide, wherein said permeabilizer peptide is bradykinin or a bradykinin analogue, and said permeabilizer peptide is effective for increasing permeability of a blood-ocular barrier to said antiviral agent.

In addition, the method pertains to the treatment of retinoblastoma, comprising administering to a patient a therapeutically effective amount of a chemotherapeutic agent and an effective amount of a permeabilizer peptide, wherein said permeabilizer peptide is bradykinin or a bradykinin analogue, and said permeabilizer peptide is effective for increasing permeability of a blood-ocular barrier to said chemotherapeutic agent.

The administration of an exogenous molecule to the host's bloodstream can be parenterally by subcutaneous, intravascular, preferably intravenous or intraarterial, by intramuscular injection, by oral administration, by eyedrops, or by any route that delivers a molecule to the bloodstream of the host. The form in which the molecule is administered (e.g., solution, emulsion, tablet, capsule, etc.) will depend, at least in part, on the route by which it is administered.

The administration of the exogenous molecule to the host's bloodstream and the administration of the permeabilizer peptide can occur simultaneously or sequentially in time. For example, a therapeutic drug can be administered orally in a tablet form while the intravascular administration of the permeabilizer is performed some time later. This allows time for the drug to be absorbed in the gastrointestinal tract and taken up by the bloodstream before the permeabilizer is given to increase the permeability of the BOB to the drug. On the other hand, the permeabilizer can be administered before or at the same time as an intravenous injection of a drug. Thus, the term "coadministration" is used herein to mean that the permeabilizer peptide and the exogenous molecule will be administered at times that will achieve significant concentrations in the blood for producing the simultaneous effects of increasing the permeability of the blood-ocular barrier to the exogenous molecule and allowing the maximum passage of the exogenous molecule from the blood to the interstitial components of the eye.

In addition, the molecule to be delivered to the eye via the bloodstream can be endogenous to the host. That is, it can be a biological product that is naturally synthesized and produced by the host. Examples of such biological products include sugars, such as glucose, and small peptides, such as enkephalins and thyroid stimulating hormone releasing factor.

An effective amount of bradykinin or a bradykinin analogue is that amount which will significantly increase the blood-ocular barrier permeability to the molecule of interest. In other words, it will increase the permeability of the blood-ocular barrier to allow sufficient quantities of a molecule of interest to pass from the blood to an ocular compartment to exert a therapeutic or prophylactic effect or allow diagnostic procedures. The effective amount will be determined on an individual basis and will be based, at least in part, on consideration of the individual's size, the specific disease, the severity of the symptoms to be treated, the result sought, the specific bradykinin analogue, the variation of individuals' affinity binding of bradykinin receptors, etc. Thus, the effective amount can be determined by one of ordinary skill in the art employing such factors and using no more than routine experimentation.

One or more permeabilizer peptides can be administered to a host in a suitable pharmaceutically acceptable carrier, any of a number of which are known to one of skill in the art. The actual amounts and concentrations of permeabilizer peptides in the compositions can be readily ascertained by a person of skill in the art.

The increase in permeability of the blood-ocular barrier in response to a permeabilizer peptide relates not only to the quantity of molecules passing from the blood into the ocular compartments, but also, to the type of molecule.

The invention is further illustrated by the following specific examples.

EXAMPLE 1

Effect of A-7 on uptake of $^{14}C$-sucrose into ocular compartments

Adult Hartley guinea pigs of either sex (250–300 g) were used. Permeabilizer A-7 was prepared by the method described in U.S. Pat. No. 5,268,164, assigned to the same assignee and hereby incorporated by reference. $^{14}C$-sucrose (560 mCi mmol$^{-1}$, New England Nuclear, Boston, Mass.) is a well accepted model molecule and was used to demonstrate permeabilization of the blood-ocular barrier by permeabilizer A-7.

Animals were anaesthetized with 6 mg/kg xylazine (Rompun®, Mobay Corp., Shawnee, Kans.) and 30 mg/kg ketamine (Vetacet®, Abeco Co., Inc., Fort Dodge, Iowa) before surgically exposing the neck vessels. The vascular eye perfusion (VEP) technique used here and previously described by Zlokovic et al. (1992, Exp. Eye Res., 54:471) allows for the study of uptake of agents in to the eye while protecting the eye from systemic metabolic changes. The technique is briefly summarized here. A fine polyethylene catheter connected to the extracorporeal perfusion system by silicon tubings was inserted into the right common carotid artery. Immediately after the start of the perfusion, the contralateral carotid artery was ligated and both jugular veins cut to allow free drainage of the perfusate.

The perfusion medium consisted of 20% washed sheep red blood cells (RBC) suspended in mock plasma of the following composition (in mM): 123 NaCl, 4 KCl, 2.5 $CaCl_2.H_2O$, 25 $NaHCO_3$, 1.2 $KH_2PO_4$, 1.8 $MgCl_2.6H_2O$ and 5.5 D-glucose. The perfusion medium was gassed with 96% $O_2$ and 4% $CO_2$ and warmed to 37.6° C., and was pumped from a reservoir through a water bath using a Rainin Rabbit peristaltic pump (Rainin Instruments, Woburn, Mass.). All tubing was low gas permeable silicon, and all metal was medical grade stainless steel. The temperature and perfusion pressure were continuously recorded, and the acid-base status frequently monitored. Perfusion pressure was kept slightly above the animal's blood pressure to eliminate any possible ingress from the systemic circulation.

Perfusion medium was delivered to the eye with or without the addition of permeabilizer A-7 (total dose of 1 µg/kg) by continuous 5 minute arterial infusions at a rate of 0.2 ml min$^{-1}$ using a Harvard syringe pump (Harvard Apparatus, South Natick, Mass.). Isotopically labeled [$^{14}C$]-sucrose was introduced into the perfusion circuit after the 5 minute infusion at a rate of 0.4 to 0.6 µCi/ml/min, over periods ranging from 1.5 min to 4.5 min. In all experiments, the perfusion was terminated by severing the right common carotid artery and decapitating the animal.

As large a sample as possible (30–40 µl) of the aqueous humor was removed with a 0.5 cc U-100 insulin syringe using 28 G ½ microfine IV needle (no dead-space), immediately after the perfusion was terminated. The eyes were enucleated and the lenses rapidly excised via a lateral approach 1.5 mm posteriorly to the limbus. The lenses were blotted on filter paper to remove any adhering aqueous humor and to avoid epithelial contamination by aqueous radioactivity. Corneas were dissected circumferentially about 0.5 mm anteriorly to the limbus. After removal of the anterior segment of the eye, the vitreous body was dissected from the retinal surface. Retinas were scooped from the lying epithelium. All tissues were blotted after dissection to minimize contamination by adjacent tissue layers and/or fluids. Samples of plasma, aqueous humor, lens, cornea, retina and posterior vitreous were treated with 2 ml Beckman Tissue Solubilizer (BTS)-450, and 16 ml of scintillant (Beckman Ready Organic, Fullerton, Calif.). Radioactivity was determined in a Beckman LS-7500 liquid scintillation spectrometer.

The data in FIGS. 2–6 and Tables I and II are expressed as ratios or percentages of tracer concentrations in different ocular fluids and tissues over that in plasma for a 4.5 minute time period in the presence or absence of A-7 (Zlokovic, supra). (When data are expressed as percentages the ratios were multiplied by 100.) The following equations were used to calculate ratios:

$C_{aqueous}$ or $C_{vitreous}/C_{plasma}$=(DPM/ml aqueous or vitreous)/(DPM/ml plasma)

$C_{lens}$ or $C_{cornea}$ or $C_{retina}/C_{plasma}$=(DPM/g lens or cornea or retina)/(DPM/ml plasma)

Shaded areas in the Figures indicate the range of error in control samples.

The unidirectional rates of transport ($K_{IN}$) of [$^{14}C$]-sucrose from the blood into the eye compartments in the presence and absence of permeabilizer A-7 were calculated for the interval between 3.0 and 4.5 minutes after addition of [$^{14}C$]-sucrose. Mathematical treatment was based on published theoretical transport model(s) (Dayson and Matchett, 1953, J. Physiol. 122:11–32; DiMattio, 1989, Invest. Ophthalmol. Vis. Sci. 30:2320–2330 and Exp. Eye Res. 49:873–885.), and the initial step of solute exchange kinetics, i.e., the unidirectional compartmental transport rates were estimated as previously reported (Zlokovic, supra). Multiple-time uptake series were performed, and the unidirectional transport rate constant, $K_{IN}$, and initial volume of tracer distribution, $V_I$, were calculated using the following equations where T is the perfusion time:

$K_{IN}$(plasma-aqueous or vitreous)=[$C_{aqueous \ or \ vitreous}$/$C_{plasma}$]T+$V_I$(aqueous or vitreous/plasma)

$K_{IN}$(plasma-lens, cornea or retina)=[$C_{lens, \ cornea \ or \ retina}$/$C_{plasma}$]T+$V_I$(lens cornea or retina/plasma)

The respective $K_{IN}$ and $V_I$ values were graphically estimated by linear regression analysis as a slope and ordinate intercept of the line corresponding to the best linear fit to experimental data points for the time period when there was no significant departure from linearity in studied compartments.

across vitreous gel, as evidenced by the uptake values that were one order of magnitude less than in the retina. A significant increase in blood-aqueous barrier permeability was obtained after 4.5 minutes of VEP (FIG. 4) that was also accompanied by increased uptake of sucrose in the lens (FIG. 5) and cornea (FIG. 6).

Figure 2:
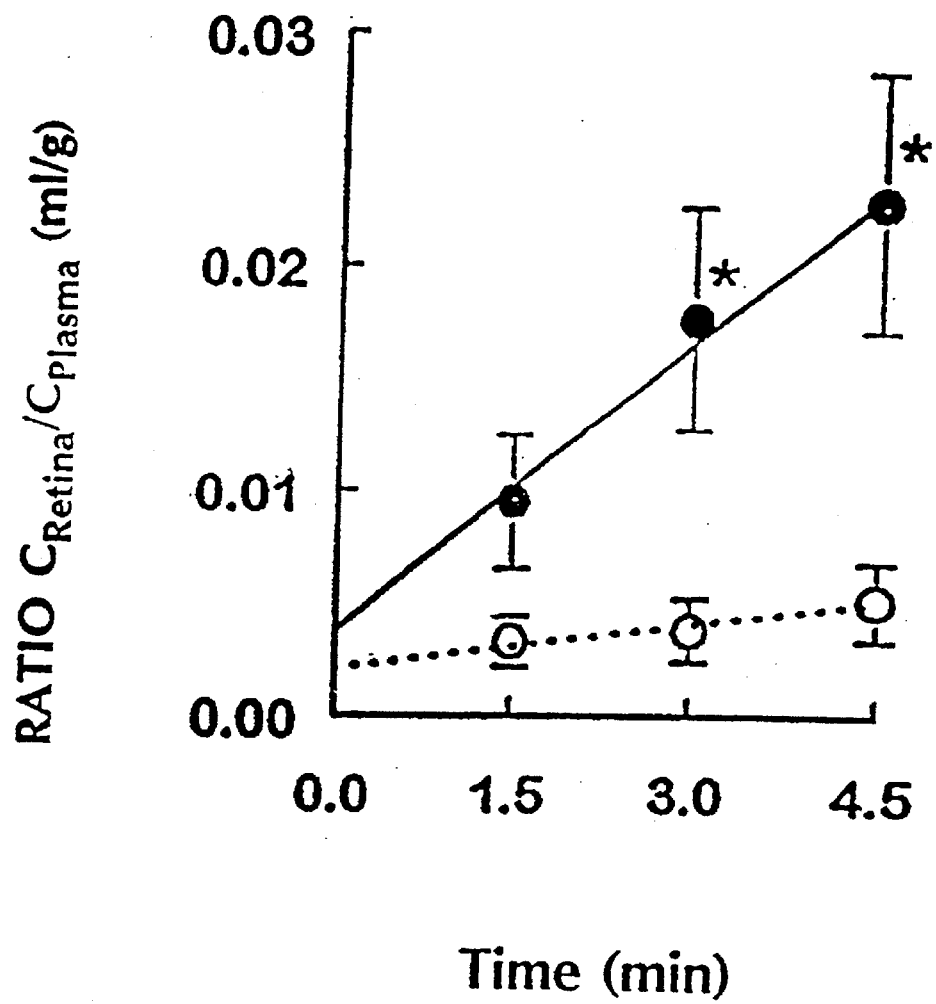
FIG. 2 is a graph showing the relative concentration of sucrose delivered to the retina in the presence (●) and absence (o) of A-7 as a function of time.
Figure 5:
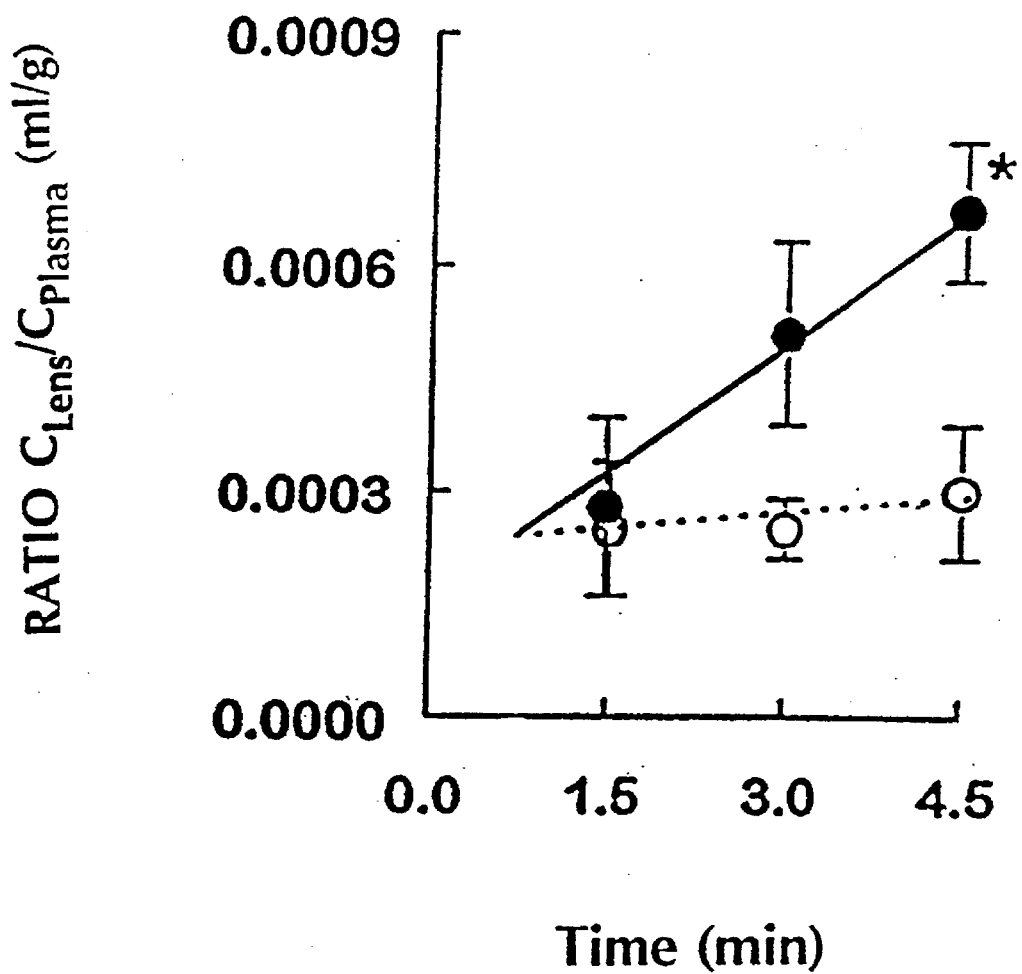
FIG. 5 is a graph showing the relative concentration of sucrose delivered to the lens in the presence (●) and absence (o) of A-7 as a function of time.
Figure 6:
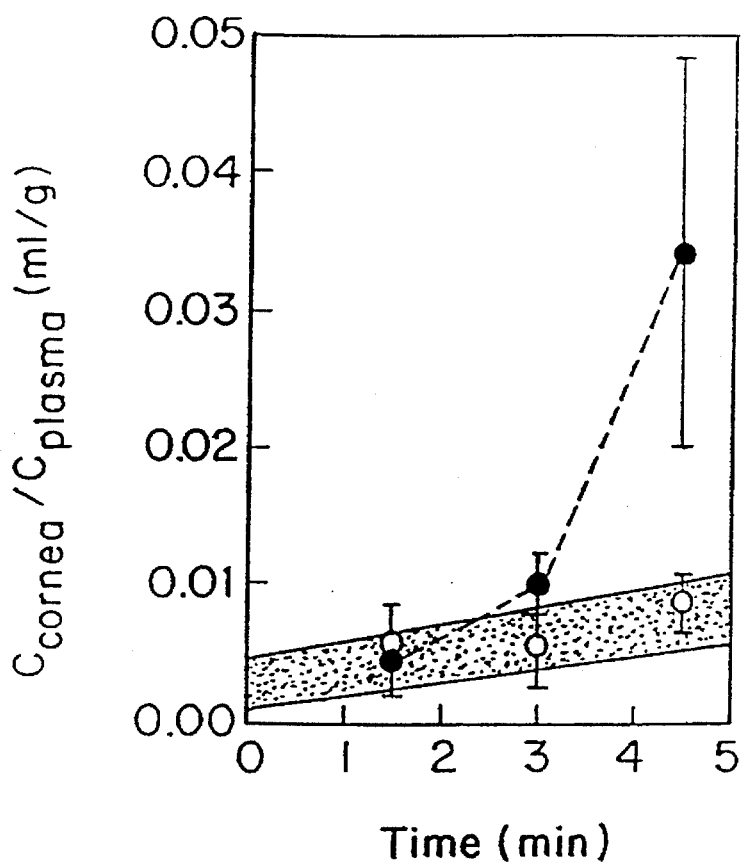
FIG. 6 is a graph showing the relative concentration of sucrose delivered to the cornea in the presence (●) and absence (o) of A-7 as a function of time.

The kinetics of sucrose entry into the retina and lens in the presence and absence of A-7 is illustrated in FIGS. 2 and 5. A-7 produced a marked increase in the initial linear slope of sucrose uptake in both tissues. The $K_{IN}$ values for sucrose in the retina and lens were 6.7 and 6.5 times higher, respectively, in the presence of A-7 (Table I). There was no initial increase in aqueous or vitreous permeability to sucrose within the first 3 minutes of VEP (Table I). However, an apparent $K_{IN}$ estimated between 3 and 4.5 minutes for aqueous permeability in the presence of A-7 was 9.13±3.66 in comparison to 1.13±0.34 μl/min/g in control animals. The control $K_{IN}$ value in vitreous was immeasurable due to extremely low uptake values, while an estimate of 0.84

TABLE I

Uptake of [$^{14}$C]-Sucrose Into the Eye

| Compartment | Treatment | % of Plasma Concentration (W/W) | | | $K_{IN}$ (μl/min/g) (3.0 min To 4.5 min) |
|---|---|---|---|---|---|
| | | 1.5 min | 3.0 min | 4.5 min | |
| | | (Time After Sucrose Added) | | | |
| Retina | Vehicle | 0.33 ± 0.08 (2) | 0.38 ± 0.14 (3) | 0.51 ± 0.16 (3) | 0.65 ± 0.25 (10) |
| | A-7 | 0.95 ± 0.30 (4) | 1.76 ± 0.50 (5) | 2.26 ± 0.56 (7) | 4.27 ± 0.9 (16) |
| | p | NS | 0.08 | <0.05 | <0.01 |
| Vitreous | Vehicle | 0.030 (1) | 0.040 ± 0.02 (5) | 0.03 ± 0.01 (5) | 0.00 ± 0.00 (10) |
| | A-7 | 0.03 ± 0.018 (4) | 0.05 ± 0.01 (6) | 0.18 ± 0.05 (7) | 0.84 ± 0.25 (13) |
| | p | NA | NS | <0.0442 | <0.001 |
| Aqueous | Vehicle | 0.33 ± 0.11 (6) | 0.33 ± 0.09 (7) | 0.50 ± 0.15 (9) | 1.13 ± 0.34 (16) |
| | A-7 | 0.19 ± 0.01 (4) | 0.41 ± 0.18 (3) | 1.79 ± 0.68 (5) | 9.13 ± 3.66 (8) |
| | p | NS | NS | 0.033 | <0.01 |
| Lens | Vehicle | 0.03 ± 0.01 (4) | 0.03 ± 0.00 (4) | 0.03 ± 0.01 (6) | 0.020 ± 0.008 (14) |
| | A-7 | 0.03 ± 0.02 (4) | 0.05 ± 0.01 (6) | 0.07 ± 0.01 (6) | 0.130 ± 0.015 (16) |
| | p | NS | NS | 0.005 | <0.001 |
| Cornea | Vehicle | 0.52 ± 0.33 (3) | 0.55 ± 0.12 (4) | 0.90 ± 0.20 (8) | 2.26 ± 0.75 (9) |
| | A-7 | 0.48 ± 0.19 (3) | 1.01 ± 0.23 (5) | 3.44 ± 1.40 (5)* | 16.20 ± 3.42 (10) |
| | p | NS | NS | 0.042 | <0.001 |

Data are expressed as mean ± SE; (n) = number of animals; NS = not significant; NA = not applicable.
*An outlier of 0.5% was not included in the statistical analysis.

Results were compared by analysis of variance (ANOVA), and multiple comparisons were corrected by the Bonferroni method (Posner, 1986, *Fundamentals of Biostatistics*, Duxbury Press, Boston, Mass.); p<0.05 was taken to be statistically significant. Results are presented as means±SE.

Table I summarizes the uptake of [$^{14}$C]-sucrose into different ocular fluids and tissues after 1.5, 3.0 and 4.5 minutes of VEP in the presence and absence of A-7 (1 μg/kg). The amount of [$^{14}$C]-sucrose in each compartment at the timepoints is expressed as the percent of the plasma [$^{14}$C]-sucrose concentration that appears in the ocular compartment (w/w; mean plus range). The unidirectional transport rate ($K_{IN}$) calculated for the 3.0 minute to 4.5 minute time period is also shown in Table I.

Figure 3:
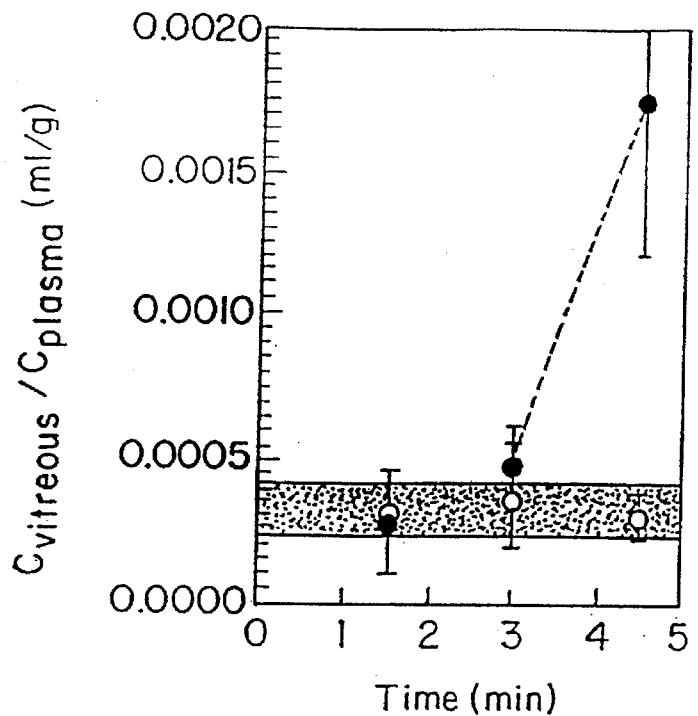
FIG. 3 is a graph showing the relative concentration of sucrose delivered to the vitreous humor in the presence (●) and absence (o) of A-7 as a function of time.
Figure 4:
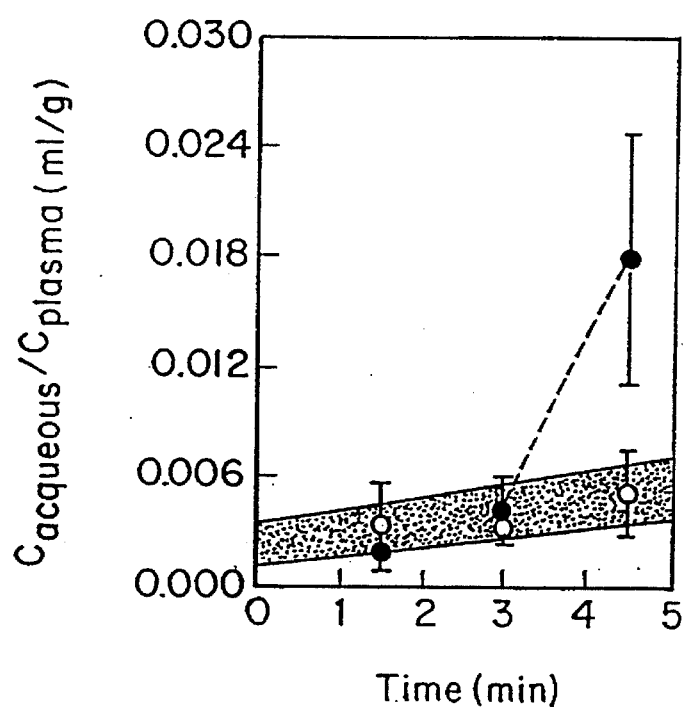
FIG. 4 is a graph showing the relative concentration of sucrose delivered to the aqueous humor in the presence (●) and absence (o) of A-7 as a function of time.

The retinal uptake of sucrose was increased by 3 to 4.5 times compared to vehicle treated control animals from 1.5 to 4.5 minutes of VEP (FIG. 2). An increase of sucrose uptake into the vitreous was also seen after 4.5 minutes of VEP. In contrast to the retina, A-7 did not affect sucrose uptake by vitreous at earlier time points (FIG. 3). The delayed effect of A-7 on the blood-vitreous barrier can possibly be explained by a lag time due to the initial sucrose diffusion across retinal layers before reaching the vitreous, as well as by a relatively slow diffusion rate of sucrose μl/min/g in the presence of A-7 was made on the basis of increase in vitreous uptake of sucrose between 3 and 4.5 minutes of VEP. In the cornea, the $K_{IN}$ values estimated between 3 and 4.5 minutes were 2.26±0.75 for control subjects and 16.20±3.42 μl/min/g for A-7 group. The differences in $K_{IN}$ values for aqueous, vitreous and cornea permeability in the presence and absence of A-7 were highly significant (P≦0.01).

EXAMPLE 2

Effect of A-7 on Physiological Functions

Increasing doses of A-7 in perfusion medium were delivered to the guinea pig eye by continuous 5 minute arterial infusions as described above. Within the first minute of infusion following administration of A-7 at 0, 1, 3 and 10 μg/kg body weight, the animals were tested for body weight, respiration rate, blood pressure (mm Hg) and heart rate. The results are shown in Table II. At 1 μg/kg A-7, the dosage used in the studies described herein, no significant changes in the designated parameters were observed.

TABLE II

Effect of A-7 on Physiological Functions

| A-7 (μg/kg Body Weight) | Body Weight (g) | Respirations/ Minute | Blood Pressure (mm Hg) | Heart Rate (Beats Per Minute) |
|---|---|---|---|---|
| Control (0) | 283 | 27 | 85 | 200 |
| (1) | 283 | 26 | 75 | 170 |
| (3) | 283 | 44 | 90 | 200 |
| (10) | 285 | 58 | 100 | Unmeasurable |

EXAMPLE 3

Effect of A-7 on uptake of [$^3$H]-ganciclovir

The methodology of these experiments is similar to that of Example 1 described above. In this case, [$^3$H]-ganciclovir (22 Ci mmol$^{-1}$, New England Nuclear, Boston, Mass.) was administered following a 5 minute arterial infusion of A-7, over periods ranging from 1.5 to 4.5 minutes. The ocular compartments were dissected as described above and analyzed for uptake of [$^3$H]-ganciclovir.

Results are shown in Table III. Retinal uptake increased two-fold compared to vehicle control from 1.5 to 4.5 minutes of VEP. A significant (1.5-2-fold) increase in uptake of ganciclovir in to the lens also occurred over the same time period. A-7 did not substantially increase ganciclovir uptake into other compartments within the measured time periods.

The $K_{IN}$ values for the retina and lens, which were calculated for the 0 to 3.0 min time period, were 2.6 and 1.3 times higher, respectively, in the presence of A-7.

was injected into the right jugular vein instead of the common carotid artery. [$^3$H]-ganciclovir was introduced following a five minute intravenous administration of A-7, and the animals were sacrificed after 1.5 or 4.5 minutes. The lenses and retinas were removed as described in Example 1.

Results are shown in Table IV. Retinal uptake of [$^3$H]-ganciclovir was increased more than 2-fold above vehicle treated controls animals (p=0.001). A significant (1.8 to 2-fold) increase in uptake into the lens also occurred over the same time period (p=0.015).

TABLE IV

UPTAKE OF [$^3$H]-GANCICLOVIR - INTRAVENOUS ADMINISTRATION

| | | % of Plasma Concentration (W/W) | |
|---|---|---|---|
| Compartment | Treatment | 1.5 min | 4.5 min |
| | | (Time After Sucrose Added) | |
| Retina | Vehicle | 3.5 ± 0.31 (6) | 4.10 ± 0.45 (9) |
| | A-7 | 3.94 ± 0.36 (5) | 8.45 ± 1.00 (10) |
| | P | NS | <0.001 |
| Lens | Vehicle | 3.12 ± 0.69 (6) | 5.47 ± 1.15 (10) |
| | A-7 | 5.46 ± 1.08 (6) | 10.01 ± 1.37 (8) |
| | P | 0.07 | <0.02 |

Data are expressed as mean (±SE); (n) = number of animals; NS = not significant.

TABLE III

Uptake of [$^3$H]-Ganciclovir Into the Eye

| | | % of Plasma Concentration (W/W) | | | |
|---|---|---|---|---|---|
| Compartment | Treatment | 1.5 min | 3.0 min | 4.5 min | $K_{IN}$ (μl/min/g) |
| | | (Time After Sucrose Added) | | | (0 min to 3.0 min) |
| Retina | Vehicle | 2.01 ± 0.22 (6) | 0.38 ± 0.36 (8) | 2.80 ± 0.3 (9) | 9.6 ± 0.9 (14) |
| | A-7 | 3.96 ± 0.68 (6) | 6.56 ± 0.79 (9) | 7.42 ± 1.14 (15) | 21.2 ± 1.5 (15) |
| | p | <0.02 | <0.02 | <0.02 | <0.01 |
| Vitreous | Vehicle | 0.03 ± 0.02 (2) | 0.04 ± 0.02 (5) | 0.1 ± 0.02 (6) | 0.4 (11) |
| | A-7 | 0.02 ± 0.00 (3) | 0.04 ± 0.03 (5) | 0.11 ± 0.04 (11) | 0.47 (16) |
| | p | NS | NS | NS | NS |
| Aqueous | Vehicle | 0.22 ± 0.03 (2) | 0.36 ± 0.07 (6) | 0.41 ± 0.1 (6) | ND |
| | A-7 | 0.46 ± 0.1 (3) | 0.51 ± 0.21 (6) | 0.55 ± 1.0 (11) | |
| | p | NS | NS | NS | |
| Lens | Vehicle | 4.10 ± 0.44 (6) | 8.07 ± 0.76 (7) | 8.22 ± 0.68 (11) | 27.5 ± 0.3 (13) |
| | A-7 | 7.89 ± 0.52 (6) | 11.86 ± 1.42 (7) | 13.37 ± 1.06 (15) | 40.3 ± 5.6 (13) |
| | p | <0.02 | <0.02 | <0.02 | <0.05 |
| Cornea | Vehicle | 0.76 (1) | 2.32 ± 0.59 (4) | 2.41 ± 0.13 (5) | 1.04 (6) |
| | A-7 | 1.16 ± 0.53 (3) | 2.98 ± 0.33 (6) | 2.92 ± 0.46 (9) | 1.21 (9) |
| | p | NA | NS | NS | NS |

Data are expressed as mean (±SE); (n) = number of animals; NS = not significant; ND = not determined; NA = not applicable.

EXAMPLE 4

Effect of A-7 on uptake of 3H-ganciclovir into the retina and lens following intravenous administration of A-7

The methodology of these experiments is similar to that of Example 1 except for the following modifications. In this case, [$^3$H]-ganciclovir (22 Ci mmol$^{-1}$, Moravek Brea, Calif.)

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

I claim:

1. A method for increasing the permeability of the blood-ocular barrier of a host to a molecule present in the bloodstream of the host thereby treating or diagnosing a disease of the eye comprising intravascularly administering to said host an effective amount of a permeabilizer peptide of said blood-ocular barrier, wherein said permeabilizer peptide comprises bradykinin or a bradykinin analogue and said permeabilizer peptide is effective for increasing blood-ocular barrier permeability to said agent.

2. A method of claim 1 wherein the host is a human.

3. A method of claim 2 wherein the bradykinin analogue comprises a peptide with the amino acid sequence NH$_2$-arginine-proline-hydroxyproline-glycine-thienylalanine-serine-proline-4-Me-tyrosine-¥(CH$_2$NH) arginine-COOH (SEQ. ID NO. 1) or a conformational analogue thereof.

4. A method of claim 1 wherein bradykinin or a bradykinin analogue permeabilizes the blood-aqueous barrier.

5. A method of claim 1 wherein bradykinin or a bradykinin analogue permeabilizes the blood-retinal barrier.

6. A method of claim 1 wherein said permeabilizer peptide of blood-ocular barrier permeability and said molecule are intravascularly co-administered to said host.

7. A method of claim 1 wherein said molecule comprises a therapeutic agent.

8. A method of claim 1 wherein said molecule comprises a diagnostic imaging agent.

9. A method of delivering a therapeutic or diagnostic agent to the eye of a patient in need of treatment or diagnosis of a disease of the eye comprising co-administering an effective amount of a permeabilizer peptide of a blood-ocular barrier, wherein said permeabilizer peptide is bradykinin or a bradykinin analog, and a therapeutic or diagnostic agent, said permeabilizer peptide being effective for increasing permeability of a blood ocular barrier to said therapeutic or diagnostic agent.

10. A method of claim 9 wherein the disease is cytomegalovirus retinitis.

11. A method of treating cytomegalovirus retinitis in the eye of a patient, comprising coadministering to the patient a therapeutically effective amount of an antiviral agent and an effective amount of a permeabilizer peptide, wherein said permeabilizer peptide is bradykinin or a bradykinin analog, and said permeabilizer peptide is effective for increasing permeability of a blood-ocular barrier to said antiviral agent.

12. A method of treating a retinoblastoma in the eye of a patient, comprising coadministering to the patient a therapeutically effective amount of a chemotherapeutic agent and an effective amount of a permeabilizer peptide, wherein said permeabilizer peptide is bradykinin or a bradykinin analog, and said permeabilizer peptide is effective for increasing permeability of a blood-ocular barrier to said chemotherapeutic agent.

* * * * *

UNITED STATES PATENT AND TRADEMARK OFFICE
CERTIFICATE OF CORRECTION

PATENT NO. : 5,585,355
DATED : December 17, 1996
INVENTOR(S) : William F. Graney It is certified that error appears in the above-indentified patent and that said Letters Patent is hereby corrected as shown below:

In Column 11, line 67: Before the word "comprising", delete the word "eve" and insert therefor --eye--.

Signed and Sealed this

Fourth Day of March, 1997

Attest:

BRUCE LEHMAN

Attesting Officer   Commissioner of Patents and Trademarks